United States Patent [19]
Nakano et al.

[11] Patent Number: 5,998,396
[45] Date of Patent: Dec. 7, 1999

[54] OIL SOLUBILIZED SOLUTIONS AND FOODS CONTAINING PHYTOSTEROLS AND PROCESS FOR THEIR PRODUCTION

[75] Inventors: Takahisa Nakano; Hidekazu Kikuchi, both of Chiba; Shinpei Itoh, Yachiyo, all of Japan

[73] Assignee: Riken Vitamin Co., Ltd., Tokyo, Japan

[21] Appl. No.: 08/956,041

[22] Filed: Oct. 24, 1997

[51] Int. Cl.⁶ .............................. A23L 1/30; A23L 1/035; A61K 31/56
[52] U.S. Cl. ........................... 514/182; 514/937; 426/601
[58] Field of Search ................................... 514/182, 937; 426/601

[56] References Cited

U.S. PATENT DOCUMENTS

| | | | |
|---|---|---|---|
| 3,085,939 | 4/1963 | Wruble | 167/65 |
| 3,865,939 | 2/1975 | Jandacek et al. | 426/601 |
| 5,244,887 | 9/1993 | Straub | 514/182 |
| 5,523,087 | 6/1996 | Shlyankevich | 424/195.1 |

FOREIGN PATENT DOCUMENTS

| | | |
|---|---|---|
| 0092076 | 10/1983 | European Pat. Off. . |
| 62-148424 | 10/1987 | Japan . |
| 931115 | 7/1963 | United Kingdom . |
| 1298047 | 1/1972 | United Kingdom . |
| 96/38047 | 12/1996 | WIPO . |

*Primary Examiner*—Frederick Krass
*Attorney, Agent, or Firm*—Roylance, Abrams, Berdo & Goodman, L.L.P.

[57] ABSTRACT

The present invention discloses oil solubilized solutions and foods containing phystosterols containing sitosterols with improved stability, for better absorption of those phytosterols into the body through their oil solubilization, as well as a process for their production; the oil solubilized solutions and foods of the invention are characterized by addition of vitamin E and emulsifiers to sitosterol-containing plant sterols to render the plant sterols soluble in oil, and particularly by extraction of the sitosterol from natural plant components, either alone or as a composition containing other phytosterol components, and by inclusion of vitamin E, emulsifiers which are liquid at room temperature, and glycerin esters of medium chain fatty acids of 6–12 carbon atoms; the process for producing oil solubilized plant sterols according to the invention is characterized by adding vitamin E and emulsifiers to phystosterols containing sitosterols to render the plant sterols soluble in oil.

27 Claims, No Drawings

OIL SOLUBILIZED SOLUTIONS AND FOODS CONTAINING PHYTOSTEROLS AND PROCESS FOR THEIR PRODUCTION

BACKGROUND OF THE INVENTION

1. Field of the Invention

The present invention relates to oil solubilized solutions and foods containing phytosterols and to a process for their production, and more specifically it relates to oil solubilized solutions and foods containing phytosterols which have improving effects on benign prostatic hyperplasia and prophylactic effects against various disease such as hiper lipidemia and the like, as well as to a process for their production.

2. Description of the Prior Art

Phytosterols such as sitosterols have long been known for their inhibiting effects on cholesterol absorption, and have been used as clinical or non-prescription drugs for improvement in hyperlipidemia. However, because phytosterols tend to be poorly soluble in oil as well as water, they have been prepared either as oil suspensions or in the form of powder or granules.

Water solubilization of phytosterols is disclosed in Japanese Laid-open Patent Publication No.Sho-50-89520 and 53-31210, but these relate to processes for producing sterol injections, not for oral administration.

It is also known that combination of phytosterols and ethylene oxide improve the solubility in water and organic solvent due to the length of the ethylene oxide chain, but this is applied for toiletries, and not for foods.

Insoluble form of phytosterols are not only poorly absorbed, but also inconvenient for common use as food additives, therefore improvements have been desired in these areas. In Germany, sitosterols have been used for symptom improvement of benign prostatic hyperplasia (see R. R. Berges, J. Windeler, H. J. Trampish, Th Senge and the β-sitosterol study group. Randomized, placebo-controlled, double-blind clinical trial of β-sitosterol in patients with benign prostatic hyperplasia. The Lancet, 345, 1529, 1995), but it is used in powder form because of its insoluble nature.

Refer to the following documents for uses of phytosterols as cholesterol-lowering agents.

A. Lees A. M., Mok H. Y. I., Lees R. S., McCluskey M. A. and Grundy S. M., Phytosterols as Cholesterol-Lowering Agents: Clinical Trials in Patients with Hypercholesterolemia and Studies or Sterol Balance., Atherosclerosis, 28, 325, 1997.

B. MATSUMOTO Shinzo. et al., Double-Blind Clinical Trials for ST-2, Shinyaku to Rinsho, 10, 2527 (1973).

C. SANO Tadahiro., Antiplatelet Effect of Unsaponifiable Soybean ST-2 (3rd Report), Rinsho to Riken, 59, 2611 (1982)

D. KAJIYAMA Goro. et al., Effect of DS-4046 on Hyperlipidemia, Yakuri to Chiryo, 16, 2965 (1988)

E. OTANI Reiji., Clinical Use Results for Sometol Against Hyperlipidemia, Yakuri to Chiryo, 12, 4155 (1984)

F. TAKEI Yoshio., Clinical Use Results for Sometol, Kiso to Rinsho, 19, 1684 (1985)

G. HATA Yoshichika. et al., Effects of Unsaponifiable Soybean (Soysterol) on Hyperlipidemia, Geriat. Med., 24, 1635 (1986)

It is an object of the present invention to provide oil solubilized solutions and foods containing phytosterols such as sitosterol, and particularly to provide oil solubilized solutions and foods containing plant sterols such as sitosterol with improved stability, for better absorption of the phytosterols into the body through their oil solubilization, as well as a process for their production.

SUMMARY OF THE INVENTION

The subject matter of the present invention is achieved by:

1. A food including a phytosterol containing sitosterol, characterized by addition of vitamin E and an emulsifier to the phytosterol containing sitosterol for solubilization of the phytosterols in oil;

2. A food according to 1, characterized in that said sitosterol is extracted from natural plant components, either alone or as a composition containing other phytosterols components;

3. A food according to 1 or 2, characterized in that the oil-solubilized phytosterol solution contains vitamin E in an amount of at least 5 wt %;

4. A food according to any of 1 to 3, characterized in that the emulsifier is a liquid emulsifier at room temperature, and is present in the oil-solubilized phytosterol solution in an amount of at least 5 wt %;

5. A food according to any of 1 to 4, characterized by containing 0–10 wt % of a glycerin ester of a medium chain fatty acid of 6–12 carbon atoms;

6. An oil-solubilized solution containing 1–50 wt % of a phytosterols containing sitosterol which is soluble in oil;

7. An oil-solubilized solution according to 4, characterized by addition of vitamin E and an emulsifier to the phytosterols containing sitosterol for solubilization of the phytosterols in oil;

8. An oil-solubilized solution according to 6 or 7, characterized in that said sitosterol is extracted from natural plant components, either alone or as a composition containing other phytosterols components;

9. An oil-solubilized solution according to 6, 7 or 8, characterized in that the oil-solubilized phytosterols solution contains vitamin E in an amount of at least 5 wt %;

10. An oil-solubilized solution according to any of 6 to 9, characterized in that the emulsifier is a liquid emulsifier at room temperature, and is present in the oil-solubilized phytosterols solution in an amount of at least 5 wt %;

11. An oil-solubilized solution according to 6, characterized by using both vitamin E and an emulsifier which is liquid at room temperature and wherein the fatty acid composition contains at least 60 wt % of oleic acid or lauric acid either alone or in combination;

12. An oil-solubilized solution according to any of 6 to 11, characterized by containing 0–10 wt % of a glycerin ester of a medium chain fatty acid of 6–12 carbon atoms; and 13. A process for producing an oil-solubilized plant sterol, characterized by adding vitamin E and an emulsifier to a phytosterols containing sitosterol for solubilization of the phytosterols in oil.

In order to achieve the object stated above, the present inventors have achieved oil solubilization of sitosterol and other phytosterols for stabilization of sitosterol to provide compositions which are readily absorbed in the human body, and have thus facilitated the processing of various types of foods. In particular, the present inventors have conducted diligent research on oil solubilization of sitosterol, and as a result have found that an oil-solubilized solution according to 7, 8 and 9 above, with simultaneous use of vitamin E and an emulsifier which is liquid at room temperature, allows preparation of stable and highly absorbable phytosterols, which has been difficult according to the prior art.

The present invention has also been completed upon the finding that addition of MCTs (glycerin esters of medium chain fatty acids of 6–12 carbon atoms, especially triglycerides) both improves the fluidity of the compositions, while also providing a better feel to the tongue and being easy to use in foods.

DETAILED DESCRIPTION OF THE PREFERRED EMBODIMENT

The present invention will now be explained in further detail.

The sitosterol to be used according to the invention is a type of phytosterol which is obtained by separation from distilate and the like generated by deodorizing processes at plant oil production factories. Sitosterol is a type of phytosterol which is a constituent of the cell membrane of plants, together with campesterol and stigmasterol, and sitosterol is the most abundant sterol in the plant.

Sterols are classified into animal, plant, microbial and marine sterols, but according to the present invention phytosterolscontaining sitosterol are effective. Known phytosterols other than those containing sitosterol include stigmasterol, campesterol and brassicasterol. Sitosterol is the most abundant sterol in the plant, and is widely found in plant seed oils and other plant parts. Stigmasterol is abundant in soybean, coconuts and cottonseed, campesterol is abundant in soybean, rapeseed and wheat, and brassicasterol is abundant in rapeseed. The sitosterol used for the invention need not be separated as a single product, and may be used in admixture with the other aforementioned sterols, etc.

The vitamin E to be used according to the present invention may be in the form of $\alpha$-, $\beta$-, $\gamma$, or $\delta$-tocopherol, and of course there is no difference in solubility even with mixtures thereof. Consequently, there is no difference in the solubility regardless of the extraction source of the vitamin E.

The emulsifier to be used according to the present invention is a liquid emulsifier at room temperature, examples of which include glycerin fatty acid esters, diglycerin fatty acid esters, polyglycerin fatty acid esters, organic acid glycerin fatty acid esters, propylene glycol fatty acid esters, sorbitan fatty acid esters and sucrose fatty acid esters, which may be used either alone or in combinations.

In addition, the emulsifier does not necessarily need to be highly purified by distillation or the like, and it may be a reaction mixture.

In particular, emulsifiers containing high concentrations of oleic acid are preferable, among which oleic acid monoglyceride, oleic acid diglyceride and oleic acid propylene glycol have high solubility and improve fluidity. The emulsifier used according to the present invention may improve the uncomfortable waxy feeling on the tongue which is characteristic of phytosterols. Therefore the compositon of the present invention can be easily used in a wide variety of foods.

MCTs to be used according to the present invention are glycerin esters of middle chain fatty acids of 6–12 carbon atoms, and are widely abundant in coconut oil. Among oils, phytosterolsdissolve most easily in MCTs, which dissolve phytosterolsup to a concentration of about 5 wt %, and MCTs with a tricaprilin (C10) composition are most suitable as they dissolve phytosterolseven up to a concentration of 7 wt %. Plant sterols will dissolve in MCTs alone up to a concentration of about 7 wt %, but the solubility is drastically improved by combination of vitamin E and an emulsifier as according to the invention. Here, the MCT can be used in a range of 0–10 wt %, but preferably 0–5 wt %. The use of MCTs according to the invention is effective both for improving the fluidity of the oil solubilized solution and for providing a much better feel to the tongue when used with the emulsifier. MCTs also help in reducing the amount of vitamin E required, and therefore the use of MCTs has high industrial significance.

According to the present invention, the oil solubilized phytosterols containing sitosterol is present in the oil- solubilized solution in an amount of 1–40 wt %, and oil-solubilized solutions containing it in amount of 15–30 wt % are easiest to use from an industrial standpoint.

Because of the low solubility of phytosterols as described above, they are almost always employed in powder or suspension form even when used as cholesterol-lowering agents or benign prostatic hyperplasia improving agents. Considering that solubility of sterols into bile acid micelles is an essential for absorption, the oil-solubilized phytosterols of the present invention are expected to be better absorbed and provide better pharmacological effects than powders or suspensions.

There are no restrictions to the foods and drinks which may contain these oil-solubilized phytosterolss, and they may include soft capsules, microcapsules, cooking oils, shortening, dressings, margarine, butter, mayonnaise, cookies, etc.

The present invention also encompasses addition of fat crystal modifiers such as lecithin, and other additives.

Embodiments of food production according to the present invention will now be provided.

Embodiment 1

Soft capsules (gelatin-glyserin capsule) were prepared from an oil-solubilized preparation having the following composition,

| | |
|---|---|
| Plant sterol (Rikesterol, Riken Vitamin Co.) | 20 wt % |
| Vitamin E (SDC-RD-50, Riken Vitamin Co.) | 50 wt % |
| Propylene glycol monooleate (Rikemal PO-100, Riken Vitamin Co.) | 30 wt % |

Embodiment 2

The following oil-solubilized preparation was made with the following composition.

| | |
|---|---|
| Plant sterol (Rikesterol, Riken Vitamin Co.) | 20 wt % |
| Vitamin E (SDC-RD-50, Riken Vitamin Co.) | 45 wt % |
| Reactive mixture of glyserol oleate (POEM OL-200, Riken Vitamin Co.) | 16 wt % |
| Propylene glycol monooleate (Rikemal PO-100, Riken Vitamin Co.) | 15 wt % |
| MCT (Actor M-2, Riken Vitamin Co.) | 5 wt % |

The oil-solubilized preparation was then used to make a dressing having the following composition.

| | |
|---|---|
| Oil-solubilized preparation | 90 g |
| Salad oil | 570 g |
| Vinegar | 250 g |
| Mustard | 1 g |
| Pepper | 1 g |
| Lemon juice | 45 g |
| Onion juice | 35 g |
| Sodium glutamate | 3 g |
| Salt | 5 g |

Embodiment 3
The oil-solubilized preparation from Embodiment 2 was used to make mayonnaise having the following composition.

| | |
|---|---|
| Oil-solubilized preparation | 90 g |
| Salad oil | 646 g |
| Vinegar | 120 g |
| Egg yolk | 100 g |
| Dispersed mustard | 20 g |
| Sodium glutamate | 2 g |
| Salt | 22 g |

Embodiment 4
The oil-solubilized preparation from Embodiment 2 was used to make margarine having the following composition.

| | |
|---|---|
| Oil-solubilized preparation | 300 g |
| Oil (liquid oil + hardened oil) | 520 g |
| Water | 148.5 g |
| Skim milk powder | 15 g |
| Salt | 14 g |
| Lecithin | 1 g |
| Flavoring | 0.49 g |
| β-carotene | 0.01 g |

Embodiment 5
The margarine prepared in Embodiment 4 was used to make cookies having the following composition.

| | |
|---|---|
| Margarine of Embodiment 4 | 200 g |
| Butter | 100 g |
| Sugar | 180 g |
| Egg white | 55 g |
| Flour | 461 g |
| Baking soda | 1 g |
| Salt | 3 g |

Effective examples of the present invention will now be provided.

Fourteen males (38–74 years of age, average 59) with a tendency to dysuria due to benign prostatic hyperplasia were asked to take soft capsules of the oil-solubilized preparation of Embodiment 1 containing 30 mg of sitosterol, at a frequency of 2 capsules 3 times a day after each meal, for a period of 3 months, and the changes in urination before and after the period were noted by autodiagnosis according to the international prostate symptom score (IPSS) shown in Table 1. The results are shown in Tables 2 to 4.

The effectiveness of the present invention was confirmed by the improved effect on dysuria due to benign prostatic hyperplasia, as shown in Tables 2 to 4.

The cookies of Example 5 also exhibited the same effect above results.

According to the present invention, there are provided compositions wherein sitosterol and other phytosterolsare stabilized by their oil solubilization for improved absorption in the human body, as well as oil solubilized solutions and foods which can be easily processed and which have an improving effect on benign prostatic hyperplasia, and a process for their production.

TABLE 1

INTERNATIONAL PROSTATE SYMPTOM SCORE (I-PSS)

| | | A | B | C | D | E | F |
|---|---|---|---|---|---|---|---|
| 1. | Over the past month, how often have you had a sensation of not emptying your bladder completely after you finished urinating? | 0 | 1 | 2 | 3 | 4 | 5 |
| 2. | Over the past month, how often have you had to urinate again less than two hours after you finished urinating | 0 | 1 | 2 | 3 | 4 | 5 |
| 3. | Over the past month, how often have you found you stopped and started again several times when you urination? | 0 | 1 | 2 | 3 | 4 | 5 |
| 4. | Over the past month, how often have you found it difficult to postpone urination? | 0 | 1 | 2 | 3 | 4 | 5 |
| 5. | Over the past month, how often have you had a weak urinary stream? | 0 | 1 | 2 | 3 | 4 | 5 |
| 6. | Over the past month, how often have you had to push or strain to begin urination? | 0 | 1 | 2 | 3 | 4 | 5 |

| | None | 1 time | 2 times | 3 times | 4 times | 5 or more times |
|---|---|---|---|---|---|---|
| 7. Over the past month, how many times did you most typically get up to urinate from the time you went to bed at night until the time you got up in the morning? | 0 | 1 | 2 | 3 | 4 | 5 |

Total I-PSS Score S =

Note:
A — None
B — Less than 1 of 5 times
C — Less than 1 of two times
D — About 1 of 2 times
E — At least 1 of 2 times
F — Almost always

TABLE 2

| | Before test | After 1 month | After 2 months | After 3 months |
|---|---|---|---|---|
| Residual urine feeling | 1.93 | 1.57 | 1.5 | 1.36 |
| Urination frequency | 2.57 | 2.07 | 1.93 | 1.5 |
| Halted urine | 1 | 1.36 | 0.79 | 0.5 |
| Postpone urine | 2 | 1.21 | 1.43 | 0.86 |
| Urinary stream | 4 | 2.93 | 2.21 | 2.21 |
| Straining | 1.71 | 1.29 | 1.07 | 0.86 |
| Nocturia | 1.64 | 1.29 | 1.43 | 1.14 |
| IPSS | 14.86 | 11.71 | 10.36 | 8.43 |

TABLE 3

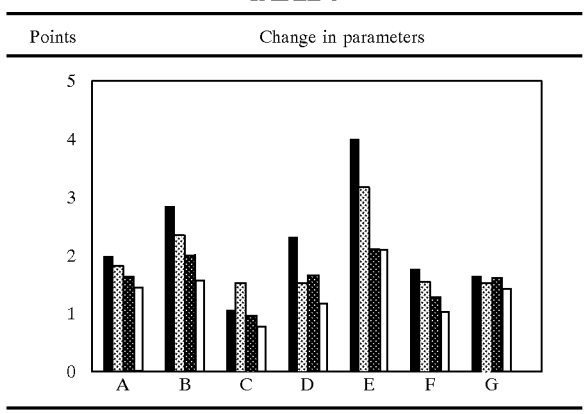

Note: Parameters
A — Residual urine feeling
B — Urination frequency
C — Halted urine
D — Urine control
E — Urine volume
F — Straining
G — Nocturnal urination ▨ Before test
▮ After 1 month
▦ After 2 months
☐ After 3 months

TABLE 4

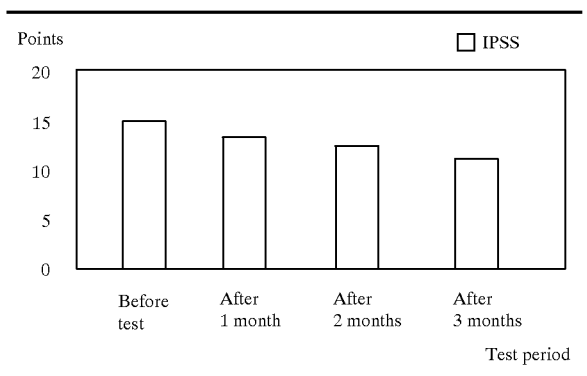

What is claimed is:

1. A composition including an edible oil, other than vitamin E, and a phytosterol-containing composition, said phytosterol-containing composition comprising:
   a phytosterol containing sitosterol;
   vitamin E;
   and an emulsifier in an amount sufficient to render said phytosterol soluble in both said vitamin E and said edible oil, with the proviso that said phytosterol is not soluble in vitamin E or said edible oil when said emulsifier is absent from the composition.

2. The composition according to claim 1, wherein said sitosterol is extracted from natural plant components, either alone or as a composition containing other phytosterol components.

3. The composition according to claim 1, wherein said composition comprises vitamin E in an amount of at least 5 wt % based on the total weight of said phytosterol, vitamin E and emulsifier.

4. The composition according to claim 1, wherein said emulsifier is a liquid emulsifier at room temperature, and is present in the composition in an amount of at least 5 wt % based on the total weight of said phytosterol, vitamin E and emulsifier.

5. The composition according to claim 1, wherein said emulsifier is a glycerin ester of a medium chain fatty acid of 6–12 carbon atoms.

6. The composition according to claim 5, wherein said composition comprises up to about 10 wt % of said glycerin ester based on the total weight of said phytosterol, vitamin E and emulsifier.

7. The composition according to claim 1, wherein said composition comprises about 1 to 50 wt % of said phytosterol based on the total weight of said phytosterol, vitamin E and emulsifier.

8. The composition of claim 1, wherein said composition comprises about 45 wt % vitamin E based on the total weight of said phytosterol, vitamin E and emulsifier.

9. The composition of claim 1, wherein said composition comprises about 50 wt % vitamin E based on the total weight of said phytosterol, vitamin E and emulsifier.

10. The composition of claim 1, wherein said composition comprises about 1–40 wt % of said phytosterol based on the total weight of said phytosterol, vitamin E and emulsifier.

11. The composition of claim 1, wherein said composition comprises about 15–30 wt % of said phytosterol based on the total weight of said phytosterol, vitamin E and emulsifier.

12. The composition of claim 1, wherein said emulsifier is selected from the group consisting of glycerin fatty acid esters, polyglycerin fatty acid esters, polyglycerin fatty acid esters, organic acid glycerin fatty acid esters, propylene glycol fatty acid esters, sorbitan fatty acid esters, sucrose fatty acid esters, and mixtures thereof.

13. A phytosterol composition that is soluble in an edible oil, other than vitamin E, said composition comprising:
   about 1 wt % to about 50 wt % of a phytosterol containing sitosterol based on the total weight of said composition;
   vitamin E; and
   an emulsifier, said emulsifier being included in an amount sufficient to render said phytosterol soluble in both vitamin E and said edible oil, with the proviso that said phytosterol is not soluble in vitamin E or said edible oil when said emulsifier is absent from the composition.

14. The composition of claim 13, wherein said composition comprises at least 5 wt % vitamin E based on the total weight of said composition.

15. The composition according to claim 13, wherein said emulsifier is a liquid emulsifier at room temperature, and is present in the composition in an amount of at least 5 wt % based on the total weight of said composition.

16. The composition according to claim 13, wherein said emulsifier is a glycerin ester of a medium chain fatty acid of 6–12 carbon atoms.

17. The composition according to claim 16, wherein said composition comprises up to about 10 wt % of said glycerin ester based on the total weight of said composition.

18. The composition of claim 13, wherein said composition comprises about 45 wt % vitamin E based on the total weight of said composition.

19. The composition of claim 13, wherein said composition comprises about 50 wt % vitamin E based on the total weight of said composition.

20. The composition of claim 13, wherein said composition comprises about 15–30 wt % of said phytosterol based on the total weight of said composition.

21. The composition of claim 13, wherein said emulsifier is selected from the group consisting of glycerin fatty acid esters, diglycerin fatty acid esters, polyglycerin fatty acid esters, organic acid glycerin fatty acid esters, propylene glycol fatty acid esters, sorbitan fatty acid esters, sucrose fatty acid esters, and mixtures thereof.

22. A process of forming a solution of a phytosterol containing a sitosterol in an edible oil, other than vitamin E, said process comprising the steps of:

forming a composition of a phytosterol containing sitosterol, vitamin E, and a liquid emulsifier, said liquid emulsifier being included in an amount sufficient to render said phytosterol soluble in both vitamin E and said edible oil, with the proviso that said phytosterol is not soluble in vitamin E or said edible oil when said emulsifier is absent from the composition; and admixing said composition with said oil and forming a solution of said phytosterol in said oil.

23. The process of claim 22, wherein said composition comprises at least about 5 wt % vitamin E based on the total weight of said composition.

24. The process of claim 22, wherein said composition comprises at least 5 wt % of said emulsifier based on the total weight of said composition.

25. The process of claim 22, wherein said emulsifier is a glycerin ester of a fatty acid having 6–12 carbon atoms and wherein said composition comprises up to about 10 wt % of said glycerin ester based on the total weight of said composition.

26. The process of claim 22, wherein said composition comprises about 1 to 50 wt % of said phytosterol based on the total weight of said composition.

27. The process of claim 22, wherein said emulsifier is selected from the group consisting of glycerin fatty acid esters, diglycerin fatty acid esters, polyglycerin fatty acid esters, organic acid glycerin fatty acid esters, propylene glycol fatty acid esters, sorbitan fatty acid esters, sucrose fatty acid esters, and mixtures thereof.

* * * * *